United States Patent [19]

Warriner

[11] Patent Number: Plant 7,573

[45] Date of Patent: Jul. 2, 1991

[54] ROSE PLANT JACTEW

[75] Inventor: William A. Warriner, Tustin, Calif.

[73] Assignee: Bear Creek Gardens, Inc., Medford, Oreg.

[21] Appl. No.: 490,842

[22] Filed: Mar. 8, 1990

[51] Int. Cl.[5] ..... A01H 5/00

[52] U.S. Cl. ..... Plt./14

[58] Field of Search ..... Plt./14, 15

*Primary Examiner*—James R. Feyrer

*Attorney, Agent, or Firm*—Klarquist, Sparkman, Campell, Leigh and Whinston

[57] ABSTRACT

A hybrid tea rose variety having heavy fragrance, unique white blending to light yellow at the center flower color, tough leathery foliage, heavy flower production, and many thorns on branches.

1 Drawing Sheet

This present invention relates to a new and distinct variety of rose plant named Jactew of the hybrid tea class which was originated by me by crossing the variety White Masterpiece, U.S. Plant Pat. No. 2,998, with the variety Sunbright, U.S. Plant Pat. No. 4,438.

The primary objective of this breeding was to produce a new rose variety having the disease resistance and heavy flowering of the male parent Sunbright, coupled with the fragrance of the female White Masterpiece. The objective was substantially achieved along with other desirable improvements as evidenced by the following unique combination of characteristics which are outstanding in the new variety and which distinguish it from its parents as well as from all other varieties of which I am aware:

1. Heavy fragrance.
2. Unique white blending to light yellow at the center flower color.
3. Tough leathery foliage.
4. Heavy flower production.
5. Many thorns on branches.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significances of color is indicated.

Parentage:

*Seed parent.*—White Masterpiece, U.S. Plant Pat. No. 2,998.

*Pollen parent.*—Sunbright, U.S. Plant Pat. No. 4,438.

Classification:

*Botanical. Rosa hybrida.*

*Commercial.*—Hybrid tea.

FLOWER

Observations made from specimens grown in a garden in Somis, Calif.

Blooming habit: Recurrent.

Bud:

*Size.*—1½ inch when the petals start to unfurl.

*Form.*—Short, pointed ovoid.

*Color.*—When sepals first divide: White Group 155D. When half bloom: Upper side of petals are White Group 155D with a definite intensifying of color to Yellow Group 12D towards the base of the flower.

*Sepals.*—Color: Green Group 138B. Surface texture: Covered in fine hairs. Three lightly appendaged sepals and two unappendaged sepals with hairy edges.

*Receptacle.*—Color: Green Group 137B. Shape: Funnel. Size: Small. Surface: Smooth.

*Peduncle.*—Length: Short. Surface: Smooth with an occasional prickle. Color: Medium green. Strength: Stiff, erect.

Bloom:

*Size.*—Large. Average open size is 4½ to 5 inches.

*Borne.*—Singly.

*Stems.*—Medium.

*Form.*—When first open: High centered. Permanence: Outer petals curl back.

*Petalage.*—Number of petals under normal conditions: 40 to 45.

*Color.*—Upper side of petals is: White Group 155D with a yellow cast to the center of the flower (Yellow Group 12D). Reverse side of petals is: Same. Base of petals is: Yellow. Major color on the upper side is: White Group 155D.

*Variegations.*—None.

*Discoloration.*—General tonality at end of first day: No change; at the end of the third day: Yellow fades more and more toward white.

*Fragrance.*—Strong.

Petals:

*Texture.*—Thick.

*Shape.*—Round, notched.

*Form.*—Tips slightly recurved.

*Arrangement.*—Imbricated. Petaloids in the center: Many.

*Persistence.*—Drop off cleanly.

*Lastingness.*—On the plant: Long. As a cut flower: Long.

Reproductive parts:

*Anthers.*—Size: Medium. Quantity: Many. Color: Reddish brown. Arrangement: Regular around styles, mixed with petaloids.

*Filaments.*—Color: White.

*Pollen.*—Color: Gold yellow.

*Styles.*—Color: Reddish.

*Stigmas.*—Color: Red.

Form: Bush.

Growth: Vigorous, upright, branching.

Foliage:

*Number of leaflets on normal mid-stem leaves.*—5.

*Size.*—Large.

*Quantity.*—Normal.

*Color.*—New foliage: Very quickly changes from red to green. Old foliage: Dark glossy green.

Leaflets:

*Shape.*—Broadly oval.

*Texture.*—Leathery, glossy.

*Edge.*—Serrated.

*Serration.*—Single, small.

*Petiole.*—Rachis: Green. Underside: Smooth.

*Stipules.*—Medium, bearded.

*Disease resistance.*—Resistant to powdery mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Many. On laterals from main canes: Many.

*Form.*—Medium, hooked slightly downward.

*Color when young.*—Green.

Small prickles:

*Quantity.*—On main stalks: Few. On laterals: Few.

*Color.*—Green.

I claim:

1. A new and distinct variety of rose plant of the hybrid tea class, substantially as herein shown and described, characterized particularly as to novelty by its heavy fragrance, high flower production, unique white with yellow at the center flower color, strong upright growth, leathery disease resistant foliage and numerous thorns.

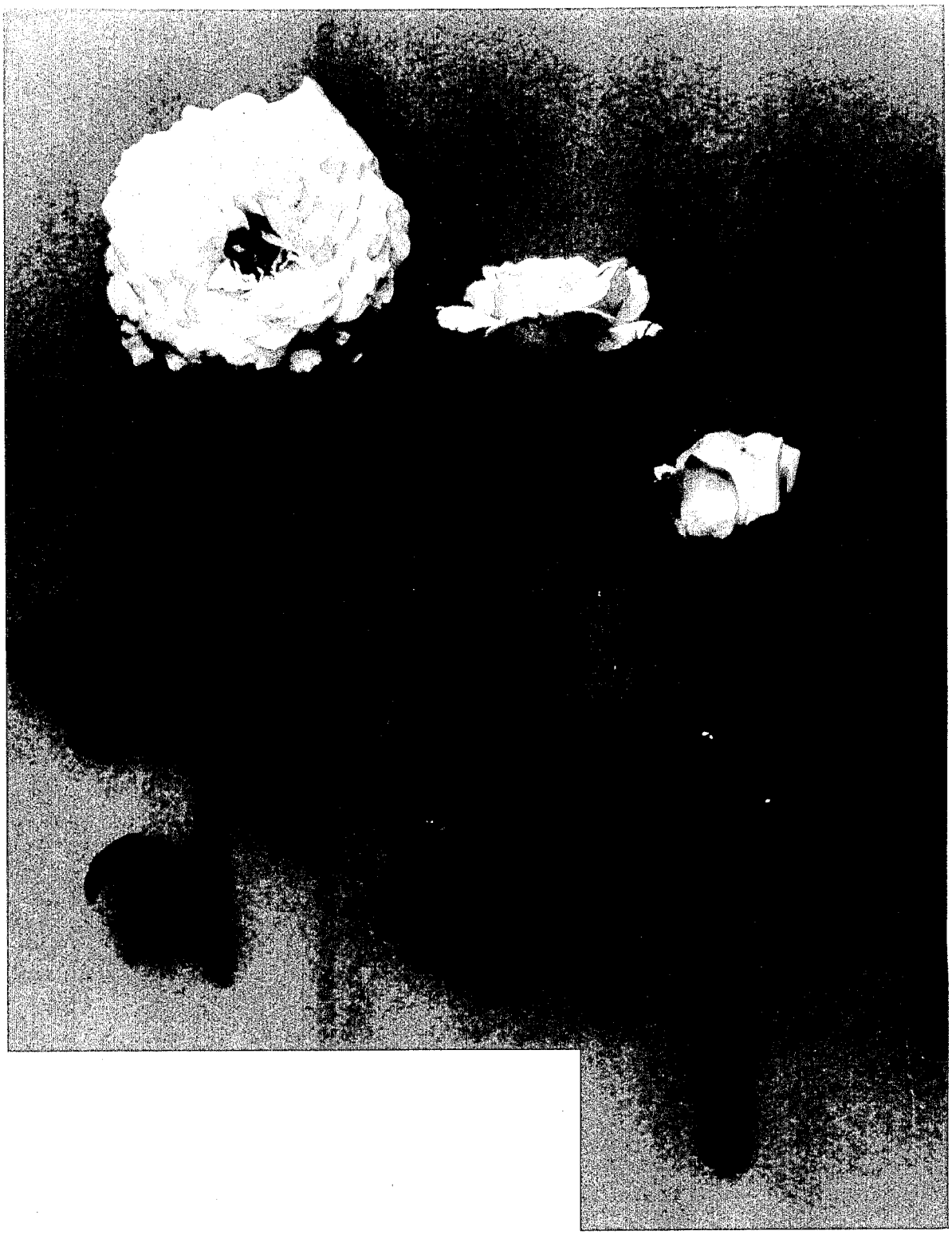

* * * * *